United States Patent [19]

Hinshaw et al.

[11] 4,306,743
[45] Dec. 22, 1981

[54] SAFETY CONNECTION FOR BREATHING TUBES

[76] Inventors: William E. Hinshaw, 1055 E. San Jose Ave., Burbank, Calif. 91501; Arnold M. Heyman, 2701 W. Alameda Ave., Burbank, Calif. 91505

[21] Appl. No.: 132,831
[22] Filed: Mar. 24, 1980
[51] Int. Cl.³ ............................................. F16L 31/00
[52] U.S. Cl. .................................. 285/260; 285/396; 285/402
[58] Field of Search ............... 285/401, 360, 361, 376, 285/402, 396, 260; 403/349

[56] References Cited

U.S. PATENT DOCUMENTS

| | | | |
|---|---|---|---|
| 788,200 | 4/1905 | Finch | 285/402 |
| 1,002,264 | 9/1911 | Gribben | 285/376 |
| 1,022,759 | 4/1912 | Stine et al. | 285/361 X |
| 1,130,726 | 3/1915 | Greve | 285/376 |
| 1,281,307 | 10/1918 | Dow et al. | 285/401 |
| 2,580,725 | 1/1952 | Breckenridge | 285/361 |
| 3,098,667 | 7/1963 | Greenwood | 285/376 |
| 3,701,548 | 10/1972 | McGuire | 285/360 X |
| 3,876,234 | 4/1975 | Harms | 285/360 X |

FOREIGN PATENT DOCUMENTS 1301318  7/1962  France ................ 285/402

Primary Examiner—Thomas F. Callaghan
Attorney, Agent, or Firm—Spensley, Horn, Jubas & Lubitz

[57] ABSTRACT

An improved connector arrangement for breathing circuit endotracheal tubes or the like in which one tube end is inserted into the other tube end. A secure connection is provided by means of a lug, groove and slot arrangement on the adjacent surfaces. When the tubes are moved axially together a lug protruding from one of the surfaces is engaged by a slot in the other and slides along the slot to a circumferential groove, thereby securing the two tubes together so that one can still be moved radially with respect to the other but not be disconnected by an inadvertent force exerted in an axial direction. A quick disconnect capability is provided by having the distance to the groove from the end of the tube along one side of the slot be less than that along the other side of the slot.

Rotation of one tube relative to the other in the appropriate direction accompanied by the application of a slight axial pulling force will cause the lug to strike the longer of the two slot walls thereby enabling a quick separation of the two tubes to be made by the subsequent application of an axial pulling force.

6 Claims, 7 Drawing Figures

SAFETY CONNECTION FOR BREATHING TUBES

BACKGROUND OF THE INVENTION

1. Field of the Invention

This invention relates to couplings for use with endotracheal tubes and other breathing circuit tubes which are used in conjunction with anaesthetic or other medical devices.

2. Description of the Prior Art

In medical devices for delivering anaesthetic or other gases to a patient, the delivery tubing and couplings are generally made of polyethylene or similar material and are attached to one another by means of a simple friction fit. The somewhat pliable material provides a relatively good gas seal, but the couplings are susceptible to becoming disconnected simply by the application of enough force to overcome the friction fit. The simplicity of the friction fit does provide a further advantage in that it enables the tubes which are coupled to be rotated with respect to one another, which may be desirable in certain instances, e.g., to reposition a tube or apparatus with respect to a patient.

During surgery, the security of connection between breathing circuit tubes becomes even more critical. With the typical friction fit tube, it has been found that during surgery it is not uncommon for the breathing circuit tubes to become disconnected. Such disconnection can result in the disruption of a critical gas supply, other extreme emergency, or even a fatality. Several different endotracheal tube connectors have been developed in order to provide increased connector security for critical applications. Such connectors are disclosed in U.S. Pat. Nos. 4,029,105 to Faust, 4,152,017 to Abramson and 3,552,778 to Muller. The devices disclosed in each of these patents employs an annular ridge on one connecting tube which cooperates with a circumferential groove on a second connecting tube. The two tubes are connected by means of a snap-fit. Although these devices provide a swivelling function which is desirable in certain instances, they may still be inadvertently disconnected by the application of excessive force. The disconnection of this type of tube however, can be somewhat awkward and thus cause discomfort to a patient. In addition, these devices are structurally complex and expensive to produce.

In addition to annular ring connectors, other connecting systems have also been developed. In U.S. Pat. No. 4,009,720 to Crandall, a first endotracheal tube having an inner and outer cannula is provided. The inner cannula has a frusto-conical shaped sealing surface to which a second tube is secured by means of a clamping mechanism. Although this system provides an air-tight seal and in addition provides for quick disconnection, it is relatively complex and its cost is therefore accordingly increased. A metal Y-piece which has a machined L-shaped slit to receive a pin welded to the metal connector of an endotracheal tube is shown in 47 *British Journal of Anaesthesia*, No. 10, 1034, (1975). Although this system provides protection against inadvertent disconnection, it does not easily accommodate rotation of the endotracheal tube and because of its metal construction, the sealing effectiveness between the connector walls is relatively low. In addition, it is non-disposable, increasing the possibility of contamination.

In the general area of tubular couplings, there are several systems which utilize a groove and lug arrangement. Such devices are disclosed in U.S. Pat. Nos. 2,795,438 to Oetiker, 2,107,165 to Rice, 437,915 to Costigan, 99,744 to Alford, 2,922,667 to Lanciano and 3,913,953 to Archer, et al. Most of these devices are directed to metal or concrete connectors and are not faced with the same sealing, safety or quick disconnect problems encountered with endotracheal tubes.

It is an object of the present invention to provide a breathing circuit or tube connector which provides a positive safety connection by means of a lug and groove arrangement. It is a further object of the present invention to provide a breathing circuit or endotracheal tube connector which maintains an effective gas seal. Another object of the present invention is to provide a breathing tube or endotracheal tube connector having a quick disconnect capability. Another object of the present invention is to provide a breathing circuit or endotracheal tube connector which is simple, inexpensive to manufacture, and disposable, thereby eliminating the hazards of contamination present in reusable apparatus.

SUMMARY OF THE INVENTION

The present invention is directed to a connector arrangement for breathing circuit tubes, endotracheal tubes or the like in which the cylindrical surfaces of the tubes are fabricated so that their surfaces mate to provide the necessary seal with the atmosphere to prevent inadvertent disconnection of the tubes, to facilitate simple disconnection and connection, and to permit rotation of one tube with respect to the other during use.

In the preferred embodiment, one of the tubes has a circumferential groove near its end extending around the tube. An access groove or slot connects this circumferential groove with the end of the tube. In the preferred embodiment the access groove is parallel with the axis of the tube. These two grooves are of such a size that they can accommodate a lug which protrudes from the cylindrical surface of the other tube a short distance from the end of the tube. When the two tubes are moved axially together, the access groove engages the lug into the circumferential groove, so that the tubes cannot be disconnected by an inadvertent axial pulling force but can still rotate with respect to one another. This feature minimizes the possibility that the two tubes will be inadvertently disconnected during a surgical or other procedure.

Another feature of the present invention is that frictional contact between the ends of the tubes is utilized to seal the interior of the connector arrangement from the atmosphere. The sealing area can be increased if desired simply by increasing the distance between the lug and the end of the tube.

In the preferred embodiment, the width of the circumferential groove is greater on one side of the access groove than on the other. From its smallest width at the first edge of the access groove the circumferential groove width increases continuously as the groove proceeds around the tube to the second edge of the access groove in such a manner that the distance between the end of the tube and the circumferential groove along the second edge is less than that along the first edge. To disconnect the tubes a slight axial pulling force is applied to the tubes while they are rotated with respect to one another so that the lug slides along the circumferential groove in the direction of increasing groove width. During this procedure the lug will pass the second edge of the access slot, strike the longer first edge and stop. At this point an axial pulling force will cause the lug to slide down the access groove to the end of the tube. This quick-disconnect feature eliminates the necessity of visually aligning the lug with the access slot in order to effect a disconnection. Alternative designs can also be employed to provide a quick-disconnect feature. For those applications where visual alignment of the lug with the access slot is acceptable, the circumferential groove can be uniform in width and exterior marks on the two tubes can be used to align the lug with the access groove.

The present invention is especially useful at the junction of Y or right angle connectors and the corrugated breathing tubes used in breathing circuit or endotracheal devices. In addition, it may be useful at the junction between breathing circuit tubes and anesthesia machines or at the junction of any two hard polyethylene plastic tubes.

At the junction of an endotracheal tube connector and the endotracheal tube itself (which is soft plastic tubing slip-fitted over an end of the connector), inadvertent disconnection can be avoided by molding screw threads into the endotracheal tube connector end. The soft plastic tubing would then be slip-fitted onto the end of the connectors and tend to collapse into the grooves of the screw thread, thereby securing the tubing to the connector. The tubing and the connector can be easily disconnected, however, by a simple pulling twist motion. A seal is maintained by either leaving the very tip of the connector end unthreaded or by sliding the tubing onto the connector so that its end extends beyond the threaded portion of the connector end.

DESCRIPTION OF THE PREFERRED EMBODIMENTS

Figure 1:
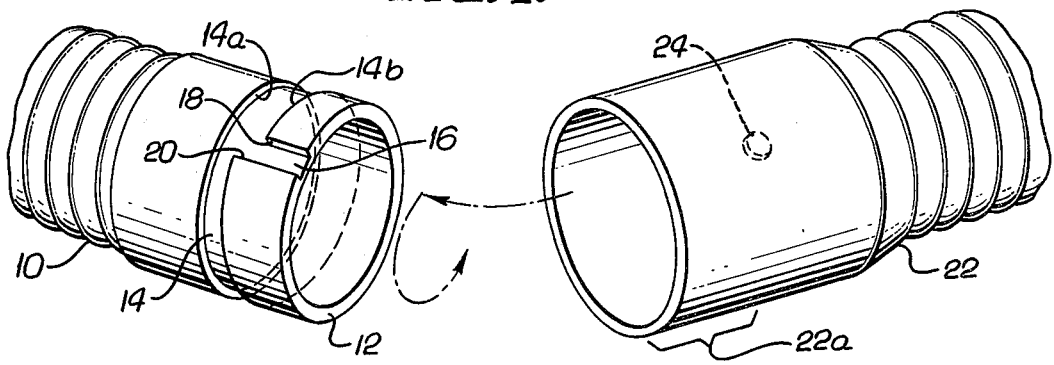
FIG. 1 is a perspective view of the connector arrangement of the present invention showing two breathing circuit tubes in a separated configuration.

Referring to FIG. 1, a first breathing circuit tube 10, which is made of polyethylene or similar material, includes a free end 12. A circumferential groove 14 is integrally formed in the outer surface of the tube 10 a short distance from the end 12. The groove 14 is coupled to the end 12 by means of an access groove 16 which is also integrally formed on the outside surface of the tube 10. The access groove 16 is defined by edges 18 and 20, with the edge 18 being shorter than the edge 20.

The width of the groove 14 gradually and continuously increases as it proceeds around the surface of the tube 10 from the edge 20 to the edge 18. In the preferred embodiment of the invention, the rear edge 14a of the groove 14 is parallel to the edge 12 of the tube 10, while the front edge 14b extends in a spiral fashion around the surface of the tube 10.

A second breathing circuit tube 22, which may also be made of polyethylene or similar material, has a smooth interior surface which fits over the outside of the tube 10. The size of the tubes 10 and 22 is such that the interior surface of the tube 22 maintains frictional engagement with the exterior surface of the tube 10 in order to provide an effective seal from the outside atmosphere. The tube 22 includes an inwardly extending lug 24 located on the inner surface of the tube 22 a short distance from the end of the tube. The size of the lug 24 is such that it can slide within the grooves 14 and 16 of the first tube. In addition, the height of the lug 24 is somewhat less than the depth of the grooves 14 and 16.

Figure 2:
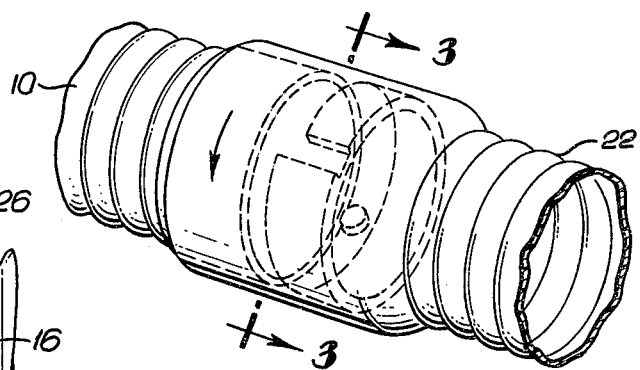
FIG. 2 is a perspective view of the breathing circuit tubes shown in a connected configuration.
Figure 4:
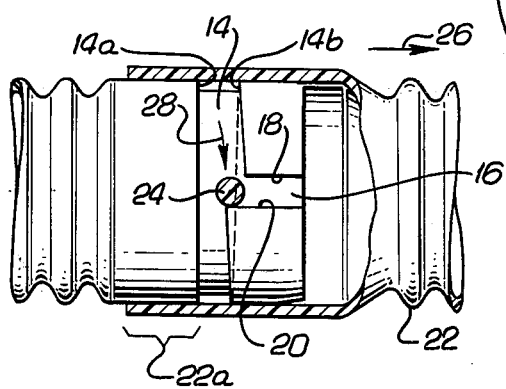
FIG. 4 is a plan view, partially in section, showing the quick-disconnect feature of the present invention.
Figure 3:
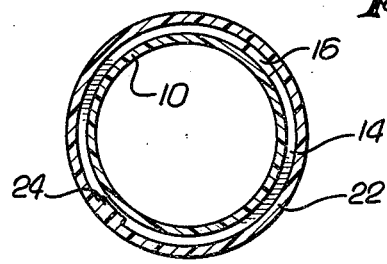
FIG. 3 is a section view taken along lines 3—3 of FIG. 2.

Referring now to FIGS. 2-4, the operation of the present invention is such that the lug 2 is aligned with the groove 16 and the tube 22 then pushed over the end of the tube 10. As the lug 24 slides within the groove 16, it would eventually contact the rear wall 14a of the groove 14. Subsequent rotation of the tube 10 relative to the tube 22 will cause the lug 24 to slide along the groove 14, so that an axial pulling force cannot separate the two tubes. Thus, the groove and lug arrangement provides a secure connection, while the friction fit between the tubes maintains an effective gas seal. The only way in which the tubes can be separated is if the lug 24 is subsequently aligned with the groove 16. Therefore, inadvertent separation of the tubes is almost completely eliminated.

Although the connection between the tubes 10 and 22 provides a seal with respect to the atmosphere by means of a frictional fit, the tubes are designed so that the amount of friction is such that it is relatively easy to rotate the tube 10 with respect to the tube 22, as may often be desired. Since the sealing function is spread over substantially the entire end portion 22a of the tube 22, a tight frictional fit is not required.

The design of the grooves 14 and 16 enables the tubes 10 and 22 to be easily and quickly disconnected from one another. As is shown most clearly in FIG. 4, by simultaneously pulling the tube 22 in a direction shown by an arrow 26 and rotating the tube 22 in a direction shown by arrow 28, the lug 24 will travel around the groove 14 along the wall 14b. When the lug 24 becomes aligned with the access groove 16, it will contact the wall 20 which will stop the rotational motion. The force applied in the direction of the arrow 26 will then cause the lug 24 to move along the groove 16, and the tubes will subsequently separate.

Figure 5:
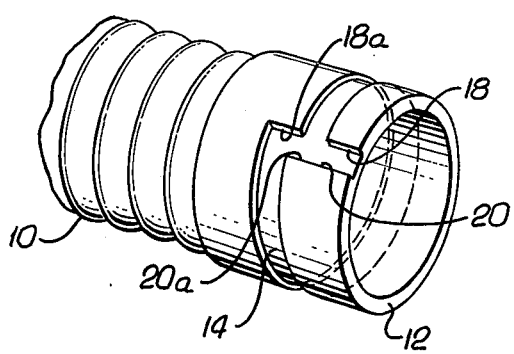
FIG. 5 is a perspective view of an alternative groove arrangement.
Figure 6:
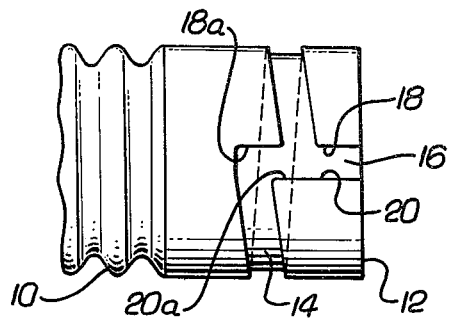
FIG. 6 is a plan view of the groove arrangement of FIG. 5.

Referring now to FIGS. 5 and 6, an alternative arrangement for the groove 14 is shown. In this embodiment, the groove 14 is formed as a spiral extending around the surface of the tube 10. Beginning from the edge 20 of the groove 16, the groove 14 spirals toward the end 12 of the tube 10. In this embodiment, the edge 18 of the groove 16 is longer than the edge 18 in its middle rather than at one end. In this embodiment, rotation of the tube 22 in either direction will be halted when the lug 24 is aligned with the groove 16. If the tube 22 is rotated in a clockwise direction, the lug 24 will eventually contact a portion 18a of the wall 18, and if the tube 22 is rotated in a counterclockwise direction, the lug 24 will contact a portion 20a of the wall 20. Thus, the arrangement of FIGS. 5 and 6 provides an even simpler quick-disconnect function than that shown in FIG. 2-4.

Figure 7:
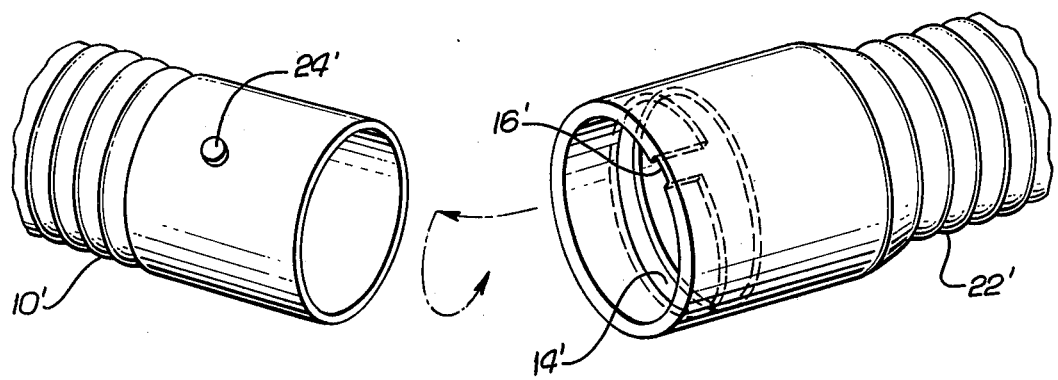
FIG. 7 is a perspective view of the connector arrangement of the present invention showing two breathing circuit tubes in a separated configuration similar to FIG. 1 but with the lug located on the outer surface of the inner tube and the grooves located on the inner surface of the outer tube.

In summary, the breathing circuit tube connector arrangement which has been described provides an effective seal against the atmosphere, enables quick and simple disconnection of the tubes, facilitates rotation of the tubes with respect to one another, and is simple and economical to manufacture. While a wide variety of materials, shapes and other configurations can be used in the invention, it should be appreciated that changes can be made without departing from the scope of the invention. For example, as shown in FIG. 7, the lug 10' could be formed on the outer surface of the tube 10' and the grooves 14' and 16' could be formed on the inner surface of the tube 22' and the same results would be obtained. Similarly, various groove configurations could be provided in order to facilitate the quick disconnection of the tubes. Therefore, although the invention has been described in terms of but two embodiments, variations and modifications will readily occur to those skilled in the art and it is intended that the claims be interpreted to cover such modifications and equivalents.

We claim:

1. An improved connecting system for breathing circuit tubes or the like, comprising:

a first tube having on one surface a radial lug located near one end and a circumferential sealing surface located nearer said one end than said lug and on the same surface;

a second tube slidably engageable with the first tube to provide a frictional connection between the ends thereof, said second tube including on one surface a generally circumferential groove extending around said second tube near one end thereof, an access groove connecting the one end of the second tube with the circumferential groove, said access groove having a sidewall intercepting said circumferential groove, and a circumferential sealing surface located further from said one end than said generally circumferential groove and on the same surface, whereby said sealing surface cooperate to seal the inside of said tubes from the environment when the tubes are secured together by initially moving the lug along the access groove to the circumferential groove and subsequently rotating one of the tubes with respect to the other so as to move the lug within the circumferential groove and away from the access groove, said tubes being freely rotatable approximately 360 degrees with respect to each other when so secured and whereby said tubes are disconnected by rotating the tubes with respect to one another until said lug contacts said sidewall of the access groove and thereafter pulling them apart.

2. The system of claim 1 wherein said lug is formed on the outer surface of the first tube and the grooves are formed on the interior surface of the second tube, whereby the first tube is insertable within the second tube.

3. The system of claim 1 wherein the distance between the edge of the circumferential groove nearest the end of the second tube and the end of the second tube decreases as the groove extends around the tube from a first side of the access groove to a second side of the access groove, whereby said second side is shorter than said first side, said configuration enabling the tubes to be quickly disconnected from one another by simultaneous application of a rotational and an axial pulling force.

4. The system of claim 1 wherein the circumferential groove spirals around the second tube from one end of one side of the access groove to the middle of the other side of the access groove, whereby the tubes can be quickly disconnected from one another by rotating the tubes with respect to one another until the lug contacts a side of the access groove and pulling the tubes apart.

5. The system of claims 3 or 4 wherein said tubes are polyethylene and the lug and grooves are integrally formed in the tubes.

6. A connector system for breathing circuit tubes or the like, comprising:

a first polyethylene tube having an integral radial lug located on the interior surface near the end of the first tube and a circumferential sealing surface on said interior surface between said lug and said end;

a second polyethylene tube having a substantially circumferential groove on the exterior surface and near the end thereof, an access groove connecting the circumferential groove with the end of the second tube and a circumferential sealing surface on said exterior surface further from said end than said circumferential groove, the distance between the end of the second tube and the side of the circumferential groove nearest the end of the tube decreasing as the circumferential groove extends around the tube from one side of the access groove to the other, whereby a first side of the access groove is longer than a second side, whereby to connect the tubes the lug is aligned with the access groove, the tubes forced together and subsequently rotated to move the lug around the circumferential groove and to disconnect the tubes they are rotated with respect to one another until the lug contacts the first side of the access groove and then pulled apart, the dimensions of said tubes being such that they provide a friction seal at said sealing surfaces against the atmosphere while allowing said tubes to rotate freely with respect to one another.

* * * * *